(12) United States Patent
Faupel et al.

(10) Patent No.: US 7,335,166 B2
(45) Date of Patent: Feb. 26, 2008

(54) SYSTEM AND METHOD FOR THE EXTRACTION AND MONITORING OF A BIOLOGICAL FLUID

(75) Inventors: Mark Faupel, Alpharetta, GA (US); Danny Lincoln, Commerce, GA (US)

(73) Assignee: SpectRx, Inc., Norcross, GA (US)

( * ) Notice: Subject to any disclaimer, the term of this patent is extended or adjusted under 35 U.S.C. 154(b) by 94 days.

(21) Appl. No.: 10/515,039

(22) PCT Filed: May 22, 2003

(86) PCT No.: PCT/US03/16315

§ 371 (c)(1),
(2), (4) Date: Jun. 2, 2005

(87) PCT Pub. No.: WO03/099123

PCT Pub. Date: Dec. 4, 2003

(65) Prior Publication Data

US 2006/0178599 A1 Aug. 10, 2006

(51) Int. Cl.
*B65D 81/00* (2006.01)
*A61B 5/00* (2006.01)

(52) U.S. Cl. .................................................... 600/578

(58) Field of Classification Search ................ 600/573, 600/575–584; 137/199; 422/101; 435/810; 604/228, 263, 405, 414; 606/181, 182
See application file for complete search history.

(56) References Cited

U.S. PATENT DOCUMENTS 4,192,919 A * 3/1980 Raghavachari .............. 600/577

| | | | |
|---|---|---|---|
| 5,047,044 A | 9/1991 | Smith et al. | |
| 5,054,499 A | 10/1991 | Swierczek | |
| 5,636,640 A | 6/1997 | Staehlin | |
| 5,680,872 A | 10/1997 | Sesekura et al. | |
| 5,843,112 A | 12/1998 | De Vaughn | |
| 6,132,449 A * | 10/2000 | Lum et al. | 606/181 |
| 6,375,626 B1 | 4/2002 | Allen et al. | |

FOREIGN PATENT DOCUMENTS

| WO | WO 93/00043 A | 1/1993 |
|---|---|---|
| WO | WO 01/54570 A | 8/2001 |

* cited by examiner

*Primary Examiner*—Max F. Hindenburg
*Assistant Examiner*—Brian Szmal
(74) *Attorney, Agent, or Firm*—Altera Law Group, LLC

(57) ABSTRACT

The systems and methods involve creating an opening in the biological tissue of the patient and placing a sampling aperture of the extraction device over the opening. The sampling aperture is defined in a contact surface of the extraction device that is placed into contact with the tissue of the patient. A pump of the extraction device such as a depressible bulb sealed to the body is charged to create a vacuum between the pump through a sampling channel to the sampling aperture, and the vacuum draws the biological fluid from the tissue opening into the sampling channel. An access point is exposed to the sampling channel, and the sample of fluid may be accessed from the access point. The access point may be an extraction opening covered by an access door, and the access door is opened to access the sample.

20 Claims, 2 Drawing Sheets

SYSTEM AND METHOD FOR THE EXTRACTION AND MONITORING OF A BIOLOGICAL FLUID

This application is being filed as a PCT International Patent application in the name of Mark Faupel and Danny Lincoln (both U.S. nationals and resident), designating all countries, on 22 May 2003.

TECHNICAL FIELD

The present invention is related to the extraction and monitoring of biological fluids. More particularly, the present invention is related to methods and systems including devices that extract biological fluids for subsequent monitoring of fluid parameters.

BACKGROUND

Biological fluids of patients such as blood, interstitial fluid, or other fluid types may be extracted and monitored by analyzing the fluid samples for various parameters. Components of a fluid sample may be analyzed to determine the current physical condition of the patient. Conventionally, the fluid sample may be taken through a sample collection device such as the Terumo CAPIJECT™.

To extract a biological fluid sample using a collection device such as the CAPIJECT™, the skin of the patient is lanced with a suitable and relatively sizable lance. The tube of the CAPIJECT™ is placed in an upright position over the relatively sizable puncture site where a drop of fluid has developed by squeezing the lanced site. A collection port of the tube is placed in proximity with the drop, and the fluid sample is then allowed to flow by gravity into the tube of the CAPIJECT™ through the collection port until the tube is filled to a recommended marking. A cap is then placed on the tube of the CAPIJECT™ to prevent the fluid sample from leaking from the tube. After taking the sample, the puncture site is treated to stop any further bleeding or other fluid loss by applying pressure to the site using a gauze pad.

Thus, while the use of the CAPIJECT™ obtains the necessary sample, there are drawbacks to its use. Notably, the patient experiences discomfort associated with the sizable puncture that is required to develop the drop of fluid. Furthermore, the puncture size must be treated as noted above to stop further fluid loss. Additionally, the puncture process recurs and a new CAPIJECT™ tube may be used each time a new sample is taken. Accordingly, the patient is inconvenienced by the extraction of biological fluid with the CAPIJECT™ device.

SUMMARY

Embodiments of the present invention address these issues and others by providing methods and devices that extract samples of biological fluids. A vacuum is created at an aperture on a surface of the device to draw fluid from the puncture into the device. The sample may then be accessed from an access point of the device for further analysis.

One embodiment is a device for extracting biological fluid. The device has a body including a contact surface that defines a sampling aperture and a sensor surface that defines an access point. The device also has a pump and a sampling channel between the sampling aperture and the pump. The sampling channel is in fluid communication with the access point.

Another embodiment is a method of extracting biological fluid. The method involves creating an artificial unobstructed opening in biological tissue. A contact surface of a sampling device is placed on the tissue, where the contact surface defines an aperture located proximate to the opening in the biological tissue. A pump of the sampling device is charged to develop a vacuum at the aperture and draw the biological fluid through the aperture into a sampling channel. The biological fluid is accessed through at an access point of the sampling device that is in fluid communication with the sampling channel.

Another embodiment is a device for extracting biological fluid. The device has a body that includes a planar contact surface that defines a sampling aperture. The device also has a sensor surface that defines an access point and a ventilation surface that defines a ventilation opening. The device also includes a depressible self-restoring bulb sealed to the body and a sampling channel between the sampling aperture and the bulb. The sampling channel is in fluid communication with the access point, and a wick is disposed within the sampling channel between the extraction opening and the bulb. A ventilation channel interconnects the ventilation opening to the sampling channel, and the wick is disposed between the ventilation chamber and the sampling aperture.

DETAILED DESCRIPTION

Embodiments of the present invention extract fluid samples from a patient by creating a vacuum over an opening on the biological tissue of the patient to draw the fluid into the device. The opening in the tissue may be of various sizes such as but not limited to relatively small openings such as a microporation puncture sites formed in the stratum corneum layer of the skin. Accordingly, the patient may experience less discomfort where such relatively small openings are created, and the relatively smaller openings in the tissue require little or no further treatment after the sample has been taken. Furthermore, upon placing the device over an opening in the tissue, the device may be fixed to the site so that multiple samples may be taken from the site over a period of time.

Figure 1:
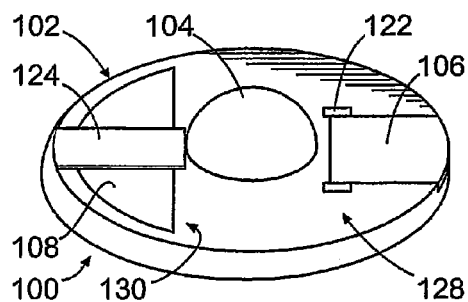
FIG. 1 is a top perspective view of an extraction device according to one embodiment.
Figure 2:
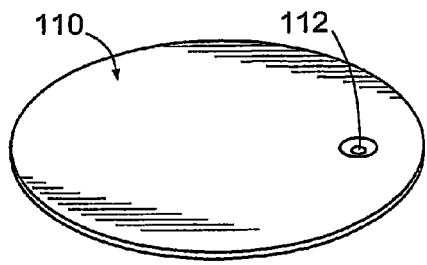
FIG. 2 is a bottom perspective view of an extraction device according to the embodiment of FIG. 1.

FIG. 1 shows one embodiment of an extraction device 100. The device includes a body 102 that provides several surfaces. The body 102 may be made of various materials, such as the Alphagary Dural 725 polyvinyl chloride ("PVC") product. Such body materials are commonly approved by government regulations for use in biomedical devices. The body may be constructed of two separate pieces to simplify the construction and the pieces are then bonded together with an adhesive. For example at top piece may define a sensor surface 128 and ventilation surface 130 while a bottom piece defines a contact surface 110 as shown in FIG. 2.

A sensor surface 128 of the body 102 defines an access point, discussed in more detail below with reference to FIG. 3, where the fluid sample may be accessed. The access point of this embodiment includes an extraction opening covered by an access door 106. The access door 106 is held in place by access door retainers 122 covering over small tabs extending from each side of the door 106. The retainers 122 are fixed to body 102 by an adhesive such as Loctite 4011 or alternatively may be integrally formed into the body 102. The access door retainers 122 hold the access door 106 in position and allow the access door to be opened and closed relative to the extraction opening. The access door 106 may be made of various materials such as the PVC used for the body 102 and a seal 134 such as silicone rubber may be placed between the access door 106 and the body 102 to form a proper seal. The access door 106 may have a snap fit to the body 102 to hold the access door 106 closed against the silicone seal.

A ventilation surface 130 of the body 102 defines a ventilation opening 118, discussed in more detail below with reference to FIG. 3, through which ventilation is provided to eliminate a vacuum created by the device 100 when the device 100 is to be removed from the patient. A ventilation plate 108 seals the ventilation opening to prevent ventilation when the vacuum is being created and sustained to draw fluid into the device 100 as discussed below. The ventilation plate 108 of this embodiment is held in place by a ventilation strap 124 that is adhesively attached to the body 102 and is removed when the ventilation plate 108 is to be removed to release the vacuum. The ventilation plate 108 and ventilation strap 124 may be made of various materials such as PVC, and a silicone rubber seal 132 may be positioned between the plate 124 and the body 102 to form a proper seal.

The extraction device 100 also includes a pump 104. In this embodiment, the pump 104 is a bulb that is sealed to the body 102 by application of an adhesive such as Loctite 4011 around the edges of the bulb. The bulb 104 is depressible and is self-restoring so that when the bulb 104 is depressed, air is forced out of the bulb and as the bulb restores its shape, a vacuum is created. The bulb 104 may be made of various resilient materials such as the ELASTOCIL® silicon rubber product. While the pump 104 is shown as a bulb, the pump 104 may be of other forms such as a syringe type pump that may be biased to self-restore the plunger position once it has been depressed or may rely on the user to restore the plunger manually to create the vacuum through the extraction device 100.

FIG. 2 shows the underside contact surface 110 of the body 102. The contact surface may be planar or may have various curvatures, depending upon the area of the body where the sample may be extracted. For example, a planar contact surface 110 is adequate where the sample is taken from the relatively flat abdomen of the patient. The contact surface 110 defines a sampling aperture 112. The sampling aperture 112 is a hole that extends from the exterior of the contact surface 110 into an internal sampling channel discussed below with reference to FIG. 3. The sampling aperture 112 may be have a countersink shape such that the hole at the exterior has a larger diameter than the channel leading from the exterior to facilitate proper placement of the aperture 112 over the puncture site.

Figure 3:
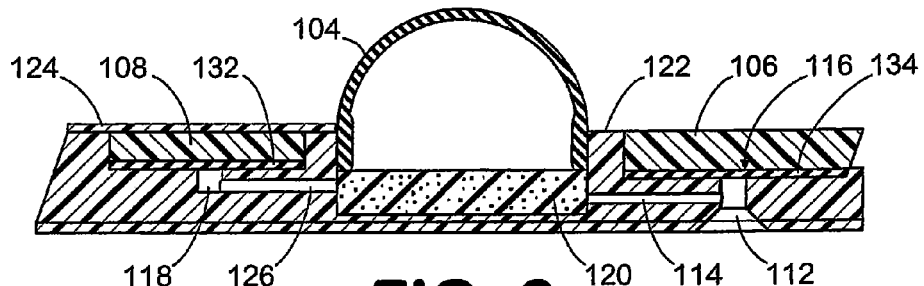
FIG. 3 is a cross-sectional view taken through the extraction device according to the embodiment of FIGS. 1 and 2.

FIG. 3 provides a cross-sectional view of the extraction device 102 as taken through the center of the bulb 104, an extraction opening 116 forming an access point, a ventilation opening 118, a wick 120, and the sampling aperture 112. As shown in this view, the interior of the bulb 104 is hollow so that the interior volume can be collapsed to evacuate the air upon the user depressing the bulb 104. The bulb collapses toward the wick 120 that allows air to pass from the bulb and out through an available channel. For example, after the device 100 is installed and the ventilation opening 118 remains sealed, the air being evacuated from the pump 104 cannot pass through the ventilation channel 126 due to the seal and cannot pass through the extraction opening 116 to ambient due to the access door 106 being closed. However, the air may pass through the sampling channel 114 and out the sampling aperture 112 to the exterior of the device 100 as the sampling aperture 112 is not sealed to the patient.

After the bulb 104 is released upon being depressed, the bulb 104 begins to restore its shape which creates a vacuum to establish suction through the wick 120, sampling channel 114, and sampling aperture 112. The vacuum causes fluid to be drawn from the opening in the tissue through the sampling aperture 112. The drawn fluid fills the portion of the sampling channel 114 up to the wick 120 but is prevented from entering the bulb 104 or the ventilation channel 126 by the wick 120. The fluid pools into the extraction opening 116. The sample can then be accessed from the access point defined by the extraction opening 116 which is in fluid communication with the sampling channel 114 upon opening the access door 106.

The wick 120 may be made of a material such as Whatman filter paper. As noted above, the wick is provided to allow air to flow while preventing the fluid from being drawn into the pump 104 and/or the ventilation chamber 126. The wick 120 thereby reduces the amount of fluid that must be sampled to produce a pool at the extraction opening 116. The wick 120 may also absorb the sample of fluid remaining after it has been satisfactorily accessed.

Figure 4:
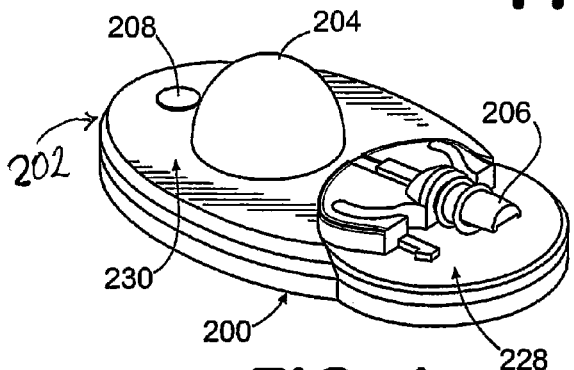
FIG. 4 is a top perspective view of an extraction device according to another embodiment.

FIG. 4 shows an alternative embodiment of the present invention. The embodiment of FIG. 4 is similar to that of FIG. 1. However, the embodiment of FIG. 4 includes a sensor connector tube and corresponding electrodes so that the fluid sample may be accessed through contact of the electrodes with the fluid. Additionally, the embodiment of FIG. 4 has a repositioned wick and sampling aperture as well as a re-routed sampling channel, and this embodiment relies on a single adhesive piece to provide the ventilation seal.

The extraction device 200 of FIG. 4 includes a body 202 that may be constructed of the materials used for the embodiment of FIG. 1. Additionally, the device 200 includes a pump 204 such as a bulb sealed to the body 202. The device 200 also includes a ventilation surface 230 of the body 202 and a ventilation cover 208 that covers a ventilation opening. The device 200 includes an sensor surface 228 that includes a tubular port 206 containing electrodes that extend into the sampling channel 214 of the body 202 to form an access point. While the tubular port 206 is shown as being integral to the body 202, the tubular port 206 and the electrode contained within it may alternatively be detachable.

Figure 5:
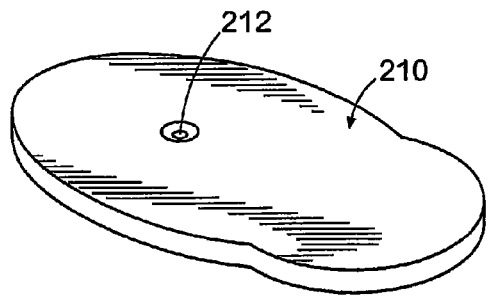
FIG. 5 is a bottom perspective view of an extraction device according to the embodiment of FIG. 4.

FIG. 5 shows the underside contact surface 210 of the device 200. As discussed above, the contact surface 210 may be planar or have a curvature. Additionally, the contact surface 210 defines a sampling aperture 212 that includes a hole at the exterior of the contact surface 210 and extends into an interior sampling channel. As discussed above, the sampling aperture 212 may have a countersink shape so that the larger diameter of the opening at the exterior facilitates placement of the aperture 212 over the opening in the tissue.

Figure 6:
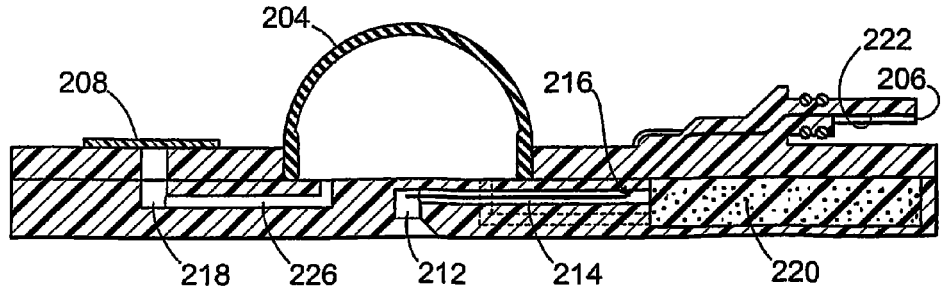
FIG. 6 is a cross-sectional view taken through the extraction device according to the embodiment of FIGS. 4 and 5.

FIG. 6 shows a cross-sectional view taken through the center of the bulb 204, a ventilation opening 218, the sampling aperture 212, the tube 206, and a wick 220. As shown in this embodiment, the wick is positioned under the sensor surface 228 of the body 202. Additionally, the sampling aperture 212 is positioned directly beneath the pump 204. However, the sampling channel 214 is routed from the base of the pump 204 to the wick 220, as indicated in phantom, and from the wick 220 to the sampling aperture 212.

The access point for accessing the fluid for testing includes the area where the electrodes enter and pass through the sampling channel 214 between the wick 220 and the sampling aperture 212. The wick 220 continues to prevent fluid from being drawn into the pump and/or ventilation channel 226 so that less fluid is necessary to remain in contact with the electrodes. Accordingly, when the pump is depressed with the ventilation seal 208 closed, air is evacuated through the sampling aperture 212 by passing from the pump 204 through the wick 220. Then, upon the pump 104 restoring its shape, a vacuum occurs and creates suction at the sampling aperture 212 so that fluid is drawn into the sampling aperture 212 and pools along the sampling channel 214 between the between the aperture 212 and the wick 220 where the electrodes are placed.

The electrodes 222 are disposed within the tube 206 and extend through into the sampling channel 214 to form the access point 216 in fluid communication with the sampling channel 214 and where the electrodes 222 access the fluid. Thus, when fluid is drawn into the sampling channel 214 and pools between the wick 220 and the sampling aperture 212, the electrodes 222 are immersed in the fluid. A sensor device (not shown) connected to the tube 206 in electrical communication with the electrodes 222 may then analyze the fluid through the exposure of the electrodes 222 to the fluid. The fluid analysis through the electrodes 222 may be performed by well-known techniques.

When the extraction device 200 is to be removed from the patient, the ventilation seal 208 may be peeled back from the ventilation opening 218 to eliminate the vacuum that has been created by passing air from ambient through the ventilation channel 226. The ventilation seal 208 may be of various forms such as an adhesive film that covers the ventilation opening 218 and that seals to the ventilation surface 230 of the body 202. The device 200 is then removed from the patient once the vacuum has been eliminated.

Figure 7:
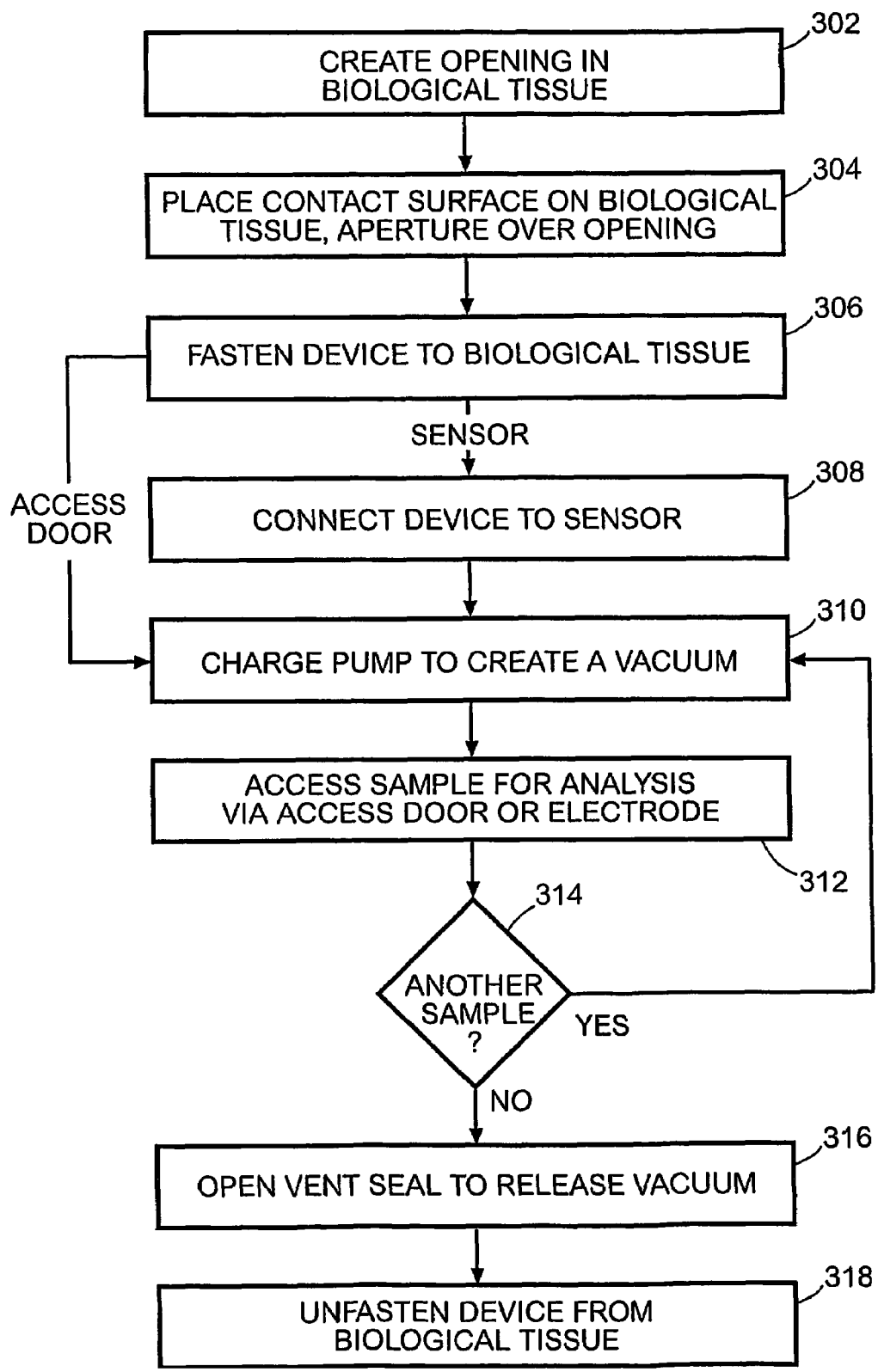
FIG. 7 illustrates a set of operations performed to extract a sample using an extraction device according to the embodiments of FIGS. 1-6.

FIG. 7 provides one example of a set of steps performed to extract samples from a patient using one of the embodiments discussed above. At opening operation 302, an artificial and unobstructed opening in the biological tissue of the patient is created. For example, the opening in the tissue may be created by a lancet, by a microporation device, by lasers, or by other techniques such as examples discussed in U.S. Pat. No. 5,885,211. The extraction device is then placed on the tissue of the patient with the sampling aperture positioned directly over the opening in the tissue at position operation 304. The extraction device is fastened to the tissue of the patient such as by taping the device to the tissue at installation operation 306. Adhesive tape may be applied to the contact surface of the extraction device such that when the device is placed on the tissue, the adhesive tape bonds to the tissue and holds the device in place. An example of such adhesive tape is ARcare® 7717.

After the device has been positioned and fastened to the tissue of the patient, the pump of the device can then be charged. For the device embodiment that includes an access door as opposed to a tube to interface with a sensor, then the pump is charged to create a vacuum at the sampling aperture at charge operation 310. For the device embodiment that includes the tube to interface with a sensor and electrodes to access the fluid, the sensor may be connected to the tube and electrodes of the extraction device at sensor operation 308, and then the pump is charged at charge operation 310.

Once the pump has been charged to create the vacuum, the fluid sample is drawn by the suction into the extraction device where it can be accessed from the access point by physically accessing the fluid through the extraction opening or can be accessed from the access point defined by the electrodes extending into the sampling channel. The fluid is accessed accordingly at sample operation 312. Then, if another sample is to be taken using the currently installed extraction device as decided at query 314, the pump is charged again at some later time at charge operation 310 to create a new vacuum and draw a new fluid sample as the older sample has been absorbed by the wick the time this next sample is to be taken.

If another sample is not to be taken using the currently installed extraction device, then the ventilation seal is removed to allow the vacuum to be eliminated at ventilation operation 316. The extraction device is then unfastened and removed from the tissue of the patient at removal operation 318. When a later sample must be taken, the process returns to the opening operation 302. The extraction device may be replaced every 2-3 days by performing the process of FIG. 7.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

What is claimed:

1. A device for extracting biological fluid from tissue having a biological opening, comprising: a body including a separate contact surface that defines a sampling aperture and a sensor surface affixable on tissue with said aperture alignable over said opening and defining an access point; a pump; and a sampling channel between the sampling aperture and the pump thereafter affixable to said contact surface, wherein the sampling channel is thereby aligned to be in fluid communication with the access point.

2. The device of claim 1, further comprising a wick disposed within the sampling channel between the access point and the pump.

3. The device of claim 2, wherein the body further includes a ventilation surface defining a ventilation opening, the device further comprising a ventilation channel interconnecting the ventilation opening to the sampling channel.

4. The device of claim 3, wherein the wick is disposed between the ventilation channel and the sampling aperture along a path of the sampling channel.

5. The device of claim 3, further comprising a ventilation seal covering the ventilation opening.

6. The device of claim 1, wherein the pump is a depressible self-restoring bulb sealed to the body.

7. The device of claim 1, wherein the access point comprises analysis electrodes extending into the sampling channel.

8. The device of claim 1, wherein the contact surface is planar.

9. A device for extracting biological fluid, comprising: a body including a contact surface that defines a sampling aperture and a sensor surface defining an access point; a pump; and a sampling channel between the sampling aperture and the pump, wherein the sampling channel is in fluid communication with the access point, and, wherein the access point comprises an extraction opening and an extraction door attached to the body and covering the extraction opening.

10. A method of extracting biological fluid from tissue having an opening, comprising: creating an artificial unobstructed opening in biological tissue; placing a contact surface of an extraction device on the biological tissue, the contact surface defining an aperture located proximate to the opening in the biological tissue; attaching an extraction pump to said contact surface after said surface is affixed to said tissue, charging a pump of the extraction device to develop a vacuum at the aperture and draw the biological fluid through the aperture into a sampling channel; and accessing the biological fluid contained within the extraction device.

11. The method of claim 10, further comprising: removing a ventilation seal covering a ventilation opening of the extraction device to allow ventilation through a ventilation chamber between the ventilation opening and the sampling channel; and removing the sampling device from the biological tissue.

12. The method of claim 10, wherein accessing the biological fluid contained within the extraction device comprises accessing the biological fluid with electrodes passing into the sampling channel.

13. The method of claim 10, wherein charging the pump of the extraction device comprises depressing a depressible self-restoring bulb sealed to the extraction body.

14. The method of claim 10, further comprising blocking the biological fluid at a wick located within the sampling channel between the pump and the sampling aperture.

15. A method of extracting biological fluid, comprising: creating an artificial unobstructed opening in biological tissue; placing a contact surface of an extraction device on the biological tissue, the contact surface defining an aperture located proximate to the opening in the biological tissue; charging a pump of the extraction device to develop a vacuum at the aperture and draw the biological fluid through the aperture into a sampling channel; and accessing the biological fluid contained within the extraction device and, wherein accessing the biological fluid contained within the extraction device comprises accessing the biological fluid through an extraction opening of the extraction device covered by an access door by opening the access door to access the extraction opening and extracting the biological fluid from the extraction opening.

16. A device for extracting biological fluid from tissue having an opening, comprising: a body including a planar contact surface that defines a sampling aperture said contact surface being independently affixable to said tissue, a separable pump unit comprising a sensor surface defining an access point, and a ventilation surface defining a ventilation opening; a depressible self-restoring bulb sealed to the body; a sampling channel between the sampling aperture and the bulb, said pump unit being affixable to said contact surface after said contact surface has been affixed to said tissue, wherein the sampling channel is in fluid communication with the access point; a wick disposed within the sampling channel between the access point and the bulb; and a ventilation channel interconnecting the ventilation opening to the sampling channel, wherein the wick is disposed between the ventilation channel and the sampling aperture along a path of the sampling channel.

17. The device of claim 16, further comprising a ventilation seal covering the ventilation opening.

18. The device of claim 16, wherein the access point comprises analysis electrodes extending into the sampling channel.

19. The device of claim 16, wherein the sampling aperture has a countersink shape.

20. A device for extracting biological fluid, comprising: a body including a planar contact surface that defines a sampling aperture, a sensor surface defining an access point, and a ventilation surface defining a ventilation opening; a depressible self-restoring bulb sealed to the body; a sampling channel between the sampling aperture and the bulb, wherein the sampling channel is in fluid communication with the access point; a wick disposed within the sampling channel between the access point and the bulb; and a ventilation channel interconnecting the ventilation opening to the sampling channel, wherein the wick is disposed between the ventilation channel and the sampling aperture along a oath of the sampling channel and wherein the access point comprises an extraction opening and an extraction door attached to the body and covering the extraction opening.

* * * * *